United States Patent [19]
Merle

[11] Patent Number: 4,911,719
[45] Date of Patent: Mar. 27, 1990

[54] JOINT PROSTHESIS
[75] Inventor: Michel Merle, Remoulins, France
[73] Assignee: Dow Corning Corporation, Midland, Mich.
[21] Appl. No.: 152,617
[22] Filed: Feb. 5, 1988
[30] Foreign Application Priority Data
  Feb. 9, 1987 [FR] France ................. 87 01516
[51] Int. Cl.⁴ .................... A61F 2/30; A61F 2/42
[52] U.S. Cl. ............................. 623/18; 623/21
[58] Field of Search ................. 623/16, 18-21
[56] References Cited
  U.S. PATENT DOCUMENTS

| | | | |
|---|---|---|---|
| 3,869,730 | 3/1975 | Skobel | 623/19 |
| 3,996,624 | 12/1976 | Noiles | 623/20 |
| 4,011,603 | 3/1977 | Steffee | 623/21 |
| 4,194,250 | 3/1980 | Walker | 623/21 X |
| 4,213,208 | 7/1980 | Marne | 623/21 |
| 4,304,011 | 12/1981 | Whelan, III | 623/21 |
| 4,352,212 | 10/1982 | Green et al. | 623/21 |
| 4,375,703 | 3/1983 | Evans et al. | 623/21 |
| 4,759,768 | 7/1988 | Hermann et al. | 623/21 |

FOREIGN PATENT DOCUMENTS 2590794 6/1987 France ..................... 623/21

Primary Examiner—Richard J. Apley
Assistant Examiner—David J. Bender
Attorney, Agent, or Firm—Allan O. Maki

[57] ABSTRACT

This invention pertains to an articulated prothesis for a joint such as for a finger. The prosthesis, capable of joining two bones, basically consists of two stems, each having a bearing component integral with one end which together form a hinged joint pivotable about an axis. A snap-on coupling integral with a hinge pin component is provided on each side of the bearing.

7 Claims, 2 Drawing Sheets

JOINT PROSTHESIS

BACKGROUND OF THE INVENTION

1. Field of the Invention

The present invention concerns prosthetic joints, that is, devices which permit replacement of damages joints and make it possible to recover the same movements which were possible with the original joints.

There exists in the human body a number of connections between bones, for example between two phalanges of a finger, which constitute joints which permit the bones to be pivoted in relation to each other, for example for closing or opening the hand. On occasion, however following accidents or certain diseases, some joints are destroyed and pivoting of the joints is no longer possible. In order to recover these movements, doctors have performed operations consisting of replacing the injured joints with prosthetic joints.

2. Description of Related Art

There are in existence numerous models for prosthetic joints, essentially matching the size and configuration of the joints to be replaced including those for joints of small dimension such as those located between two phalanges of a finger or between metacarpals and phalanges. One type for use in small joints is composed of a single piece of a flexible elastomeric material which is divided essentially into three functional parts; actually two ends connected by a hinge section. The two ends are designed to be implanted in the two bones to be connected, and the hinge section is positioned between the two bones. Since the hinge section is made of a relatively flexible material, pivoting of the two bones in the plane of the hinge can be achieved. In some cases, this structure may be subject to wear after prolonged contact with the bone surfaces.

SUMMARY OF THE INVENTION

It is the object of the present invention to ameliorate this inconvenience in particular and to obtain a joint prosthesis which is durable over extended use, easy to fabricate, relatively inexpensive to fabricate, and which can be adapted readily to all sizes of bone joints.

More precisely, the present invention pertains to a joint prosthesis adapted to reunite two elements such as bones, characterized by the fact that it comprises:

a first lever comprising a stem portion at the end of which is located a first rotary bearing a second lever comprising a second stem portion at one end of which is located a second rotary bearing, means for coupling said two bearings so that they can rotate relative to each other about an axis, and means for attaching the two stem portions to the resected bones of the joint.

Other characteristics and advantages of the present invention will appear from the description which follows the attached drawings, all of which should be considered illustrative but not limiting to the scope of the invention, wherein:

BRIEF DESCRIPTION OF THE DRAWINGS

FIGS. 1, 2, 4A and 4B show the same embodiment of the joint prosthesis, and the reference numerals indicate the same elements in each figure.

DESCRIPTION OF THE PREFERRED EMBODIMENTS

Figure 1:
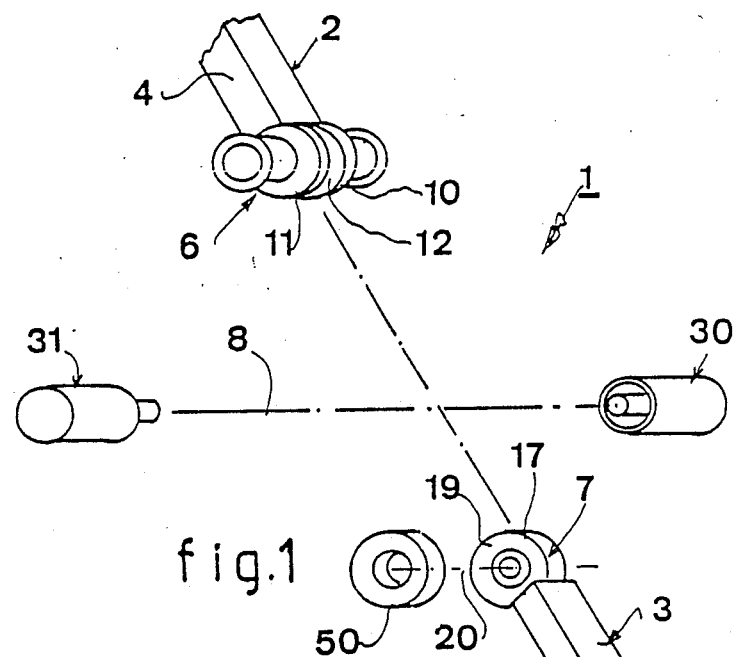
FIG. 1 represents in enlarged perspective of an embodiment of a joint prosthesis of the invention, with the components separated.
Figure 2:
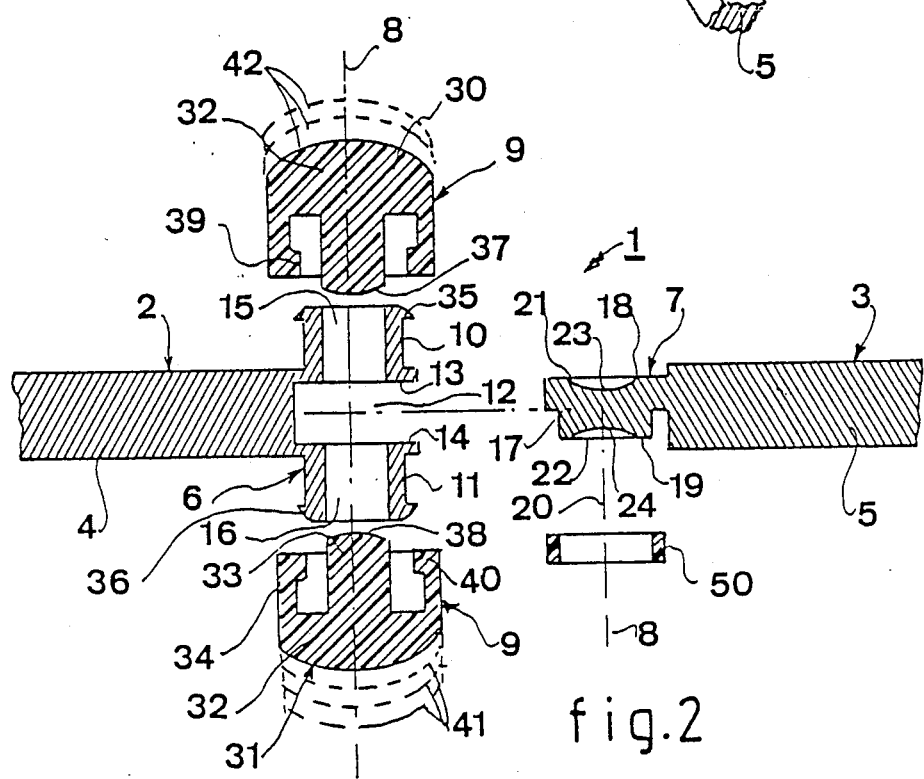
FIG. 2 represents in an enlarged sectional view of the hinge portion of the prosthesis of FIG. 1.

In FIGS. 1 and 2 are seen the same embodiment of a joint prothesis. This prosthesis comprises two stem portions 2 and 3. Each stem portion, 2, 3 respectively comprises a body 4, 5 elongated form and, at each extremity of said body, a rotating bearing 6 and 7. The two bearings 6 and 7 are adapted to cooperate by rotating one against the other so as to pivot around a single axis 8.

The prosthesis 1 moreover includes means 9 for coupling the two bearings. It will be apparent that this coupling arrangement serves to keep stabilized but free to pivot relative to each other around axis 8. FIGS. 1 and 2 show an embodiment illustrating two bearing portions 6 and 7 and coupling means 9. One of the bearings (bearing 6) includes two bushings or collars 10 and 11 integral with the stem 4, which collars define a space 12 between them constituting a recess bounded by two essentially parallel faces 13 and 14. Each collar 10, 11 includes from side to side, a cylindrical bore, 15 and 16 respectively which form the bearing for rotatable shafts 37 and 38.

In this embodiment, the second bearing 7 consists of a planar part 17 matching the space 12 so that the part 17 can pivot inside the space, thereby allowing the two virtually parallel faces 18, 19 bounding the planar part 17 to slide on the faces 13, 14 defined above. Furthermore, each face 18, 19 has a cylindrical depression 21, 22 the axis 20 of which is the same and the diameter of which should, for optimum results, be virtually identical to that of the two bores, 15, 16.

In the preferred embodiment, the cylindrical cutouts 21, 22 are recessed and do not interact, each thus having a bottom 23, 24 that serves as a surface for reacting the pressure loading exerted by the coupling means described below.

The depressions 21, 22 are so designed that their central axes of revolution 20 coincide with the axis 8 of the bores 15, 16 when the part 7 is inserted on the space 12.

In the embodiment shown, the mechanism 9 for coupling the two bearings consists of two snap-on caps 30, 31 which can have three components; a hub 32, a hinge pin component 33 integral with the hub and with a diameter matched to the bores 15, 16 and to the depressions 21 and 22, and a snap-on type retaining ring 34 designed to snap over the protruding shoulders or lips 35 and 36 on the circumference of the two collars 10, 11 defined above.

An operational articulated prosthesis 1 can easily be constructed using the components described above by arranging the two stem portions 2 and 3 such that the bearing 7 is inserted in the space 12 of the bearing 6. The two caps are designed to allow the shaft sections 33 to slide into the bores 15, 16 until ends 37, 38 abut against the bottoms 23, 24 of the depression 21, 22. The shaft sections are sufficiently long to cause this abutment before the inner shoulders 39, 40 of each retaining ring 34 are forced over the matching shoulders 35 and 36. However, as the caps are made out of a relatively resilient material, they can be deformed and the shoulders 39, 40 snapped over the protruding lips 35, 36. The inherent elasticity provides a solid coupling between bearings 6, 7.

This articulated prosthesis embodiment is particularly advantageous because it is stable and adaptable to various joints. Depending on the width of the bones being joined, a single lever layout can be used but with several types of caps, primarily in terms of the thickness of the hub 32, so that the cap ends 41, 42 can be aligned with the projection of the bone lateral edges to protect the joints adequately, as will be explained with reference to FIGS. 4A and 4B.

As described above, the two stems 2, 3 are designed to pivot relative to each other by means of bearings 6, 7. The rotation of both the bearings may be facilitated by inserting a low friction washer 50 between one of the sliding surface pairs 13, 18 or 14, 19. The washer shall match the shape of one of the two faces of the bearing 7 so that it is sandwiched between the two bearings, thereby acting as a lubricant for their relative rotation.

It is advantageous to make the levers, the caps and the washer, when applicable, out of compatible materials to prevent any biodegradation and/or parasitic chemical reactions between components of the implant. The following pairs of materials have been specially selected for the stems and the caps respectively: cobalt chrome/polyethylene, titanium/polyethylene, ceramic/polyethylene, ceramic/ceramic, TCF/TCF (registered trade name of Robert Bosch Gmbh, Stuttgart Germany for carbon fiber reinforced thermoset triazin resin.), TCF/ceramic and composite/composite materials.

Figure 3:
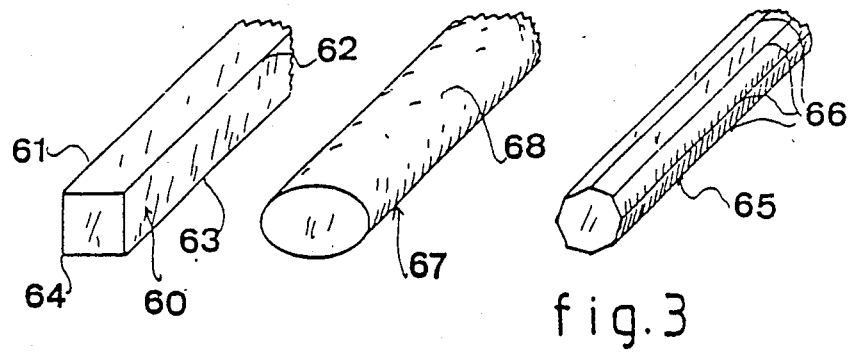
FIG. 3 represents 3 embodiments of different stem portions which may be used in connection with the invention.

The bodies 4, 5 of stems 2, 3 are designed to be inserted into sleeves secured in the bone ends being joined. Each sleeve features a cavity in which the bodies 4, 5 of the two levers 2, 3 can move in a single degree of freedom (i.e. translation) with perhaps a very small lateral play. To this end, the cavity cross-section will closely match that of the stem, which sould be selected, for the best results, from the shapes shown in FIG. 3.

Body 60 has a square cross-section with four edges 61, 62, 63, 64. Body 65 comprises another embodiment having a polygonal cross-section with eight edges 66. The third embodiment 67 has an oval cross-section, which is the optimum shape insofar as it has no sharp edges on its circumference and prevents creep within the sleeve. When the body must only have a single degree of freedom with respect to the sleeve (i.e. translation), the stem must not be of a shape which permits rotation.

Figure 4A:
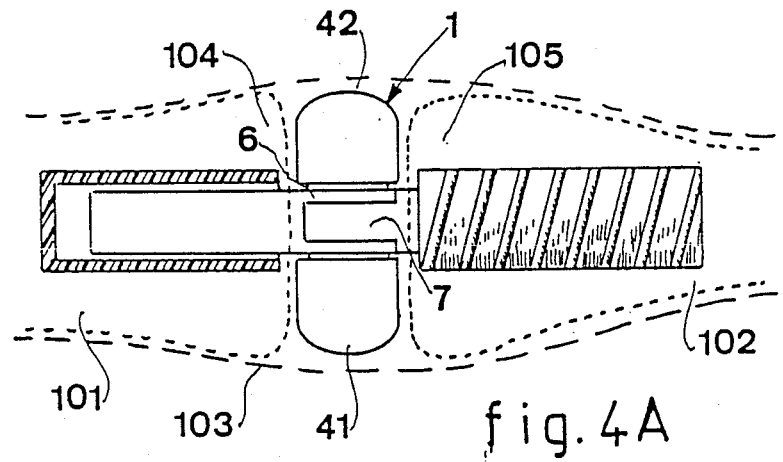
FIGS. 4A and 4B are cross sectional side views of a prosthesis of this invention which has been implanted, showing the joint in the fully extended and flexed positions, respectively.
Figure 4B:
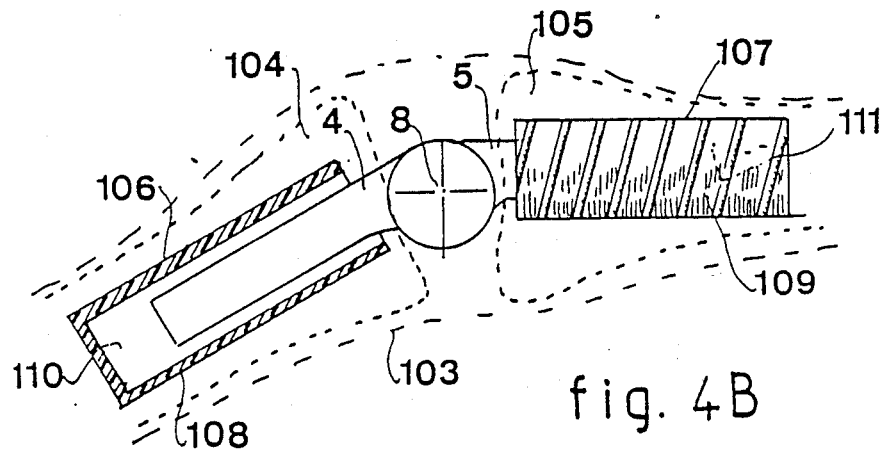

FIGS. 4A and 4B represent a typical application of an articulated prosthesis for joining two bones 101 and 102, (e.g. two bones in a finger 103 of a hand).

Cavities 106 and 107 are cut out of the free ends 104, 105 of a finger bone. Sleeves 108 and 109, which has a cavities 110 and 111 with cross-sections matching closely that of the two bodies, 4, 5 of stems 2, 3 in the articulated prosthesis 1, are secured (e.g. by screwing, bonding, etc.) in these cavities. FIG. 4A illustrates the coupling of the bearings 6, 7 of the two stems, with the caps 30, 31 press-fitted and snapped over the collars 10, 11 of the bearing 6.

Moreover this Figure indicates that the ends 41, 42 of both collars are virtually aligned with the projection of the lateral edges of the two phalanges, at least along the axis 8. In certain cases, the shape of these caps may be modified to provide peripheral continuity. It is thus possible, with one structure for levers 2, 3 and a series of different length and shaped caps, to construct articulated protheses for any width of bone, thereby contributing to the low cost of such a prosthesis compared to protheses hithertofore available.

This structure endows the articulated prosthesis pursuant to this invention with another important advantage, in particular when it is used as a joint between two finger bones on the hand. It is apparent that, when such a prosthesis is implanted in the hand, the other vital elements in the hand (i.e. nerves, tendons, etc.) must be left intact. The tendons act like a harness between the two phalanges 104, 105. This means that, when a person fitted with such a prosthesis, lifts a load, the two phalanges are subjected to a tensile force tending to move them apart and acting against the counter-reaction exerted by the tendons, thereby causing the bodies 4, 5 to slide slightly in sleeves 108. Although subject to a tensile force, the bodies do not transmit this loading to the sleeves so that the latter are not liable to be loosened from the bone, as sometimes happened with the formerly available prosthesis. This characteristic will help to give the prosthesis pursuant to this invention a far longer operational life and to make them far less likely to attack the tissue system, compared to previous prostheses, since the bones will not be degraded by extraction loads.

That which is claimed is:

1. An articulated prosthesis for implantation to join two bones comprising:
    a first stem portion having a first bearing component integral with the distal end thereof, said first bearing comprising two collars which are spaced apart from and axially aligned with each other and which together define a space bounded by two opposite and parallel faces of the internal ends of said collars, said collars being provided with cylindrical bores therethrough,
    a second stem portion having a second bearing component integral with the proximal end thereof and pivotably connected to said first bearing component, said second bearing component comprising a part having planar outside surfaces capable of fitting into said space and which contains a cylindrical depression on each side, so designed that when the second bearing component is fitted into the aforesaid space to form a hinge, the central axis of said depressions are in alignment with the axis of rotation of the bores of said collars;
    a shaft being positioned in each of said bores, one of said shafts engaging each of said depressions, and means to retain said shafts in place in such engagement.

2. A prosthesis according to claim 1, wherein each depression is dish-shaped and provided with a bottom which forms a thrust surface.

3. A prosthesis according to claim 1, wherein said shaft comprises a cap consisting of three parts including a hub, a shaft section integral with said hub, and a retaining ring integral with said hub, said ring having an internal shoulder, there being a protruding lip around the exterior outside end of each collar integral with said collar, said shoulders and said lips being configured so that the shoulder on each retaining ring can be located on the lip of said collar when said shaft section is inserted in the bore of the collar and into one of said depressions.

4. A prosthesis according to claim 3, wherein the length of the said shaft section is such that the end thereof abuts against the bottom of said depression immediately before said shoulder reaches the protruding lip.

5. A prosthesis according to claim 1, wherein at least one lubricating washer is positioned between said bearing components.

6. A prosthesis pursuant to claim 1 wherein the aforesaid stems have oval cross-sections.

7. Joint prosthesis comprising two pins each designed to be directly or indirectly inserted into a respective one of the two bones to be joined and, operative between said pins, articulation surfaces comprising, in the case of one of the pins, herein referred to for convenience as the carrier pin, two domes centered on an axis perpendicular to said carrier pin, oriented in opposite directions relative to each other and carried by said carrier pin and, for the other of said pins, herein referred to for convenience as the carried pin, two further domes each complementary to a respective one of the first-mentioned domes and thus adapted to be engaged therewith, carried by said carried pin, this joint prosthesis being generally characterized in that the domes of the carrier pin are carried by respective pegs which are movable transversely relative to the two pins, said carrier pin comprising two arms each having two respective aligned housings in which said pegs are slidably inserted.

* * * * *